US008470322B2

(12) United States Patent
Mateo De Acosta Del Rio et al.

(10) Patent No.: US 8,470,322 B2
(45) Date of Patent: Jun. 25, 2013

(54) ANTI SULFATIDES AND ANTI SUFATED PROTEOGLYCANS ANTIBODIES AND THEIR USE

(75) Inventors: Cristina Mateo De Acosta Del Rio, C. Habana (CU); Ana Maria Vazquez Lopez, C. Habana (CU); Alejandro Lopez Requena, C. Habana (CU); Yuniel Fernandez Marrero, C. Habana (CU); Yosdel Soto Lopez, C. Habana (CU); Victor Brito Navarro, C. Habana (CU)

(73) Assignee: Centro de Inmunologia Molecular, Habana (CU)

( * ) Notice: Subject to any disclaimer, the term of this patent is extended or adjusted under 35 U.S.C. 154(b) by 0 days.

(21) Appl. No.: 13/264,105

(22) PCT Filed: May 3, 2010

(86) PCT No.: PCT/CU2010/000002
§ 371 (c)(1),
(2), (4) Date: Jan. 23, 2012

(87) PCT Pub. No.: WO2010/127642
PCT Pub. Date: Nov. 11, 2010

(65) Prior Publication Data
US 2012/0121605 A1    May 17, 2012

(30) Foreign Application Priority Data
May 4, 2009  (CU) .................................. 2009-0071

(51) Int. Cl.
*A61K 39/395*    (2006.01)
*G01N 33/53*    (2006.01)
*C07K 16/46*    (2006.01)
*C07K 16/28*    (2006.01)

(52) U.S. Cl.
USPC ...................... 424/133.1; 424/143.1; 435/7.1

(58) Field of Classification Search
None
See application file for complete search history.

(56) References Cited

U.S. PATENT DOCUMENTS

2003/0100508 A1* 5/2003 Simon et al. ................... 514/14
2004/0253233 A1* 12/2004 Del Rio et al. ............. 424/142.1

FOREIGN PATENT DOCUMENTS

EP        1 411 064 A2    4/2004
WO       2008046724 A1    4/2008

OTHER PUBLICATIONS

Fernández-Marrero et al. Switching on cytotoxicity by a single mutation at the heavy chain variable region of an anti-ganglioside antibody. Molecular Immunology 48 (2011) 1059-1067.*
Brito et al. Active Immunization for Preventing Ischemic Heart Disease. Canadian Journal of Cardiology, (Oct. 2010) vol. 26, No. Suppl. D, pp. 46D. Abstract 119.*
Nakashima Yutaka et al: "Early atherosclerosis.in humans: role of diffuse intimal thickening and extracellular matrix proteoglycans." Cardiovascular Research Jul. 1, 2008 LNKD-PUBMED:18430750, vol. 79, No. 1, Jul. 1, 2008, Páginas14-23, XP009137187 ISSN: 0008-6363 Resumen; p. 19-20; fig. 5.
Radhakrishnamurthy B et al: "A Monoclonal Antibody That Recognizes Hyaluronic Acid Binding Region of Aorta Proteoglycans" Atherosclerosis, Elsevier Ireland Ltd, IE LNKD- DOI:10.1016/0021-9150(93)90127-0, vol. 98, No. 2, Jan. 25, 1993,Paginas 179-192, XP000577781 ISSN: 0021-9150 Resumen; Figuras.
Lark M W et al: "Arterial chondroitin sulfate proteoglycan: localization with a monoclonal antibody." The Journal of Histochemistry and Cytochemistry : Official Journal of the Histochemistry Society Oct. 1988 LNKD PUBMED:3047228, vol. 36, No. 10, Oct. 1988, Paginas 1211-1221, XP009137185 ISSN: 0022-1554 Resumen; Figuras.
Sobue M et al: "Production and Characterization of Monoclonal Antibody to Dermatan Sulfate Proteoglycan" Journal of Histochemistry and Cytochemistry, vol. 36, No. 5, 1988, Paginas479-486, XP009137175 ISSN: 0022-1554 Resunmen; fig. 2B.
Lopez-Requena A et al: "Chimeric anti-N-glycolyl-ganglioside and its anti-idiotypic MAbs: Immunodominance of their variable regions" Hybridoma and Hybridomics 200308 US, vol. 22, No. 4, Aug. 2003, Paginas 235-243, XP009137195 ISSN: 1536-8599 Todo el documento.
Brito et al., "Induction of Anti-Anti-Idiotype Antibodies Against Sulfated Glycosaminoglycans Reduces Atherosclerosis in Apolipoprotein E-Deficient Mice", Arterioscler Thromb Vasc Biol., 2012, 32, pp. 2847-2854.

* cited by examiner

*Primary Examiner* — Maher Haddad
(74) *Attorney, Agent, or Firm* — Rothwell, Figg, Ernst & Manbeck, P.C.

(57) ABSTRACT

The present invention relates to the biotechnology and particularly with new products for use in human health.
The present invention provides new specific monoclonal antibodies, which bind with high affinity sulfatides and sulfated proteoglycans.
The anti sulfatides and anti sulfated proteoglycans antibodies disclosed in the present invention and described in the description, provide important diagnostic and therapeutic tools to act on pathological processes associated with the appearance of atherosclerotic plaques.
Accordingly, the invention provides pharmaceutical compositions comprising MAbs of the invention or fragments thereof for the therapeutic and diagnostic use associated with cardiovascular diseases. Particularly, the present invention relates to the fragments derived from the MAbs that recognize sulfatides and sulfated proteoglycans, which can be used in the therapy or diagnosis of this pathology.

9 Claims, 3 Drawing Sheets

SEQUENCE LISTING

```
<160> NUMBER OF SEQ ID NOS: 14

<210> SEQ ID NO 1
<211> LENGTH: 5
<212> TYPE: PRT
<213> ORGANISM: Unknown
<220> FEATURE:
<223> OTHER INFORMATION: by DNA recombinant technology

<400> SEQUENCE: 1

Arg Tyr Ser Val His
1               5

<210> SEQ ID NO 2
<211> LENGTH: 16
<212> TYPE: PRT
<213> ORGANISM: Unknown
<220> FEATURE:
<223> OTHER INFORMATION: by DNA recombinant technology

<400> SEQUENCE: 2

Met Ile Trp Gly Gly Gly Ser Thr Asp Tyr Asn Ser Ala Leu Lys Ser
1               5                   10                  15

<210> SEQ ID NO 3
<211> LENGTH: 14
```

```
<212> TYPE: PRT
<213> ORGANISM: Unknown
<220> FEATURE:
<223> OTHER INFORMATION: by DNA recombinant technology

<400> SEQUENCE: 3

Ser Gly Val Arg Arg Gly Arg Ala Gln Ala Trp Phe Ala Tyr
1               5                   10

<210> SEQ ID NO 4
<211> LENGTH: 11
<212> TYPE: PRT
<213> ORGANISM: Unknown
<220> FEATURE:
<223> OTHER INFORMATION: by DNA recombinant technology

<400> SEQUENCE: 4

Lys Ala Ser Gln Asp Val Ser Thr Ala Val Ala
1               5                   10

<210> SEQ ID NO 5
<211> LENGTH: 7
<212> TYPE: PRT
<213> ORGANISM: Unknown
<220> FEATURE:
<223> OTHER INFORMATION: by DNA recombinant technology

<400> SEQUENCE: 5

Ser Ala Ser Tyr Arg Tyr Thr
1               5

<210> SEQ ID NO 6
<211> LENGTH: 9
<212> TYPE: PRT
<213> ORGANISM: Unknown
<220> FEATURE:
<223> OTHER INFORMATION: by DNA recombinant technology

<400> SEQUENCE: 6

Gln Gln His Tyr Ser Thr Pro Trp Thr
1               5

<210> SEQ ID NO 7
<211> LENGTH: 30
<212> TYPE: PRT
<213> ORGANISM: Unknown
<220> FEATURE:
<223> OTHER INFORMATION: by DNA recombinant technology

<400> SEQUENCE: 7

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser
            20                  25                  30

<210> SEQ ID NO 8
<211> LENGTH: 14
<212> TYPE: PRT
<213> ORGANISM: Unknown
<220> FEATURE:
<223> OTHER INFORMATION: by DNA recombinant technology

<400> SEQUENCE: 8

Trp Val Arg Gln Pro Pro Gly Lys Gly Leu Glu Trp Leu Gly
1               5                   10

<210> SEQ ID NO 9
```

```
<211> LENGTH: 32
<212> TYPE: PRT
<213> ORGANISM: Unknown
<220> FEATURE:
<223> OTHER INFORMATION: by DNA recombinant technology

<400> SEQUENCE: 9

Arg Leu Ser Ile Ser Lys Asp Asn Ser Lys Ser Gln Val Phe Leu Lys
1               5                   10                  15
Met Asn Ser Leu Gln Thr Asp Asp Thr Ala Met Tyr Tyr Cys Ala Arg
            20                  25                  30

<210> SEQ ID NO 10
<211> LENGTH: 11
<212> TYPE: PRT
<213> ORGANISM: Unknown
<220> FEATURE:
<223> OTHER INFORMATION: by DNA recombinant technology

<400> SEQUENCE: 10

Trp Gly Gln Gly Thr Leu Val Thr Val Ser Ala
1               5                   10

<210> SEQ ID NO 11
<211> LENGTH: 23
<212> TYPE: PRT
<213> ORGANISM: Unknown
<220> FEATURE:
<223> OTHER INFORMATION: by DNA recombinant technology

<400> SEQUENCE: 11

Asp Ile Val Met Thr Gln Ser His Lys Phe Met Ser Thr Ser Val Gly
1               5                   10                  15
Asp Arg Val Ser Ile Thr Cys
            20

<210> SEQ ID NO 12
<211> LENGTH: 15
<212> TYPE: PRT
<213> ORGANISM: Unknown
<220> FEATURE:
<223> OTHER INFORMATION: by DNA recombinant technology

<400> SEQUENCE: 12

Trp Tyr Gln Gln Lys Pro Gly Gln Ser Pro Lys Leu Leu Ile Tyr
1               5                   10                  15

<210> SEQ ID NO 13
<211> LENGTH: 32
<212> TYPE: PRT
<213> ORGANISM: Unknown
<220> FEATURE:
<223> OTHER INFORMATION: by DNA recombinant technology

<400> SEQUENCE: 13

Gly Val Pro Asp Arg Phe Thr Gly Ser Gly Ser Gly Thr Asp Phe Thr
1               5                   10                  15
Phe Thr Ile Ser Ser Val Gln Ala Glu Asp Leu Ala Val Tyr Tyr Cys
            20                  25                  30

<210> SEQ ID NO 14
<211> LENGTH: 10
<212> TYPE: PRT
<213> ORGANISM: Unknown
<220> FEATURE:
<223> OTHER INFORMATION: by DNA recombinant technology
```

```
<400> SEQUENCE: 14

Phe Gly Gly Gly Thr Lys Leu Glu Leu Lys
1               5                   10
```

ANTI SULFATIDES AND ANTI SUFATED PROTEOGLYCANS ANTIBODIES AND THEIR USE

CROSS REFERENCE TO RELATED APPLICATION

This application is a 35 U.S.C. 371 National Phase Entry Application from PCT/CU2010/000002, filed May 3, 2010, which claims the benefit of Cuban Patent Application No. 2009-0071 filed on May 4, 2009, the disclosures of which are incorporated herein in its entirety by reference.

TECHNICAL FIELD

The present invention relates to new monoclonal antibodies (MAb) that recognize specifically and with high affinity sulfatides and sulfated proteoglycans. Also the present invention relates to pharmaceutical compositions comprising monoclonal antibodies of the invention or fragments derived from these antibodies. Additionally, the present invention relates to a kit of reagents useful in the diagnosis of cardiovascular diseases comprising Abs of the invention or fragments thereof.

PREVIOUS ART

After more than 30 years of the development of hybridoma technology for obtaining murine MAb (Koehler y Milstein Nature, 256: 495-497, (1975), they have proved to be very useful in disease diagnosis and basic research, but only 20 Abs have been registered for human therapy (Pharma Vitae, Monoclonal Abs Update, 6-363, 2008) This has been largely due to their short half-life in blood and the poor recognition of murine effector functions by the human immune system, and also by the immune response due to the murine origin of these Abs when they are injected in patients (HAMA response, acronym of human anti-mouse Abs). Several studies have shown that after administration of a foreign antibody, the immune response produced in the patient may be considerably strong and can eliminate substantially the therapeutic usefulness of the antibody after initial treatment. Moreover, after giving a patient a murine MAb, subsequent treatments with unrelated mouse Abs may not be effective or even dangerous due to the cross-reactive HAMA response, according to the report of Khazaeli, M. B. y col. Journal of Immunotherapy 15: 42-52 (1994).

From the above information it becomes necessary to obtain versions of therapeutic Abs that are less immunogenic in humans, which are obtained easily and economically and that are suitable for the manufacture of therapeutic formulations and other uses. Morrison S. L. y col. Adv Immunol., 44: 65-92 (1989).

Several methods have been developed to humanize Abs from mouse or rat and thus reduce xenogeneic response against these foreign proteins when injected in humans. One of the first attempts to reduce the immunogenicity has been the generation of "chimeric" Abs, in which the variable domains of murine proteins are attached to constant domains of human molecules, accomplishing not only a reduced immunogenicity, but also the activation of immune effector functions. Morrison S. L. y col. PNAS USA, 81: 6851-6855 (1984). These chimeric molecules maintain the features of the original antibody in relation to antigen binding while its constant region is not immunogenic.

Atherosclerosis and its consequences have a huge impact on the world's population and are the leading cause of morbidity and mortality in developed countries (Melián, A. y col. Am. J. Pathol., 155:775, 1999) and in Cuba from several years ago (OMS, 2004, Anuario Estadistico, MINSAP, 2007).

Atherosclerosis is a chronic inflammatory disease of multifactorial nature that greatly contributes to the pathogenesis of myocardial and brain infarction, gangrene, and loss of limb functions. Greaves, D. R. y col. Trends Immunol 22: 180-181 (2001); Ross, R. y col. Am Heart J 138(5 Pt 2): S419-20 (1999).

One of the leading causes of atherosclerosis is hypercholesterolemia. Low molecular weight lipoproteins (LDL) in transit through the arterial wall are trapped in the extracellular matrix of the arterial intima, by interactions with proteoglycans, and undergo oxidative modifications. Lipoproteins bound to proteoglycans of the arterial intima are more susceptible to changes in both the lipid and protein moieties, such as oxidation and enzymatic hydrolysis, which increases their atherogenic potential. ApoB-100 contains several regions through which it can bind to glycosaminoglycan chains of proteoglycans, having in common the presence of multiple basic amino acids. Camejo, G., E. y col. Atherosclerosis 139: 205-22, (1998); Chang, T. Y. y col. Curr Opin Lipidol 12: 289-96 (2001); Camejo, G., U. y col. Atheroscler Suppl 3: 3-9 (2002).

The density of negative charges on glycosaminoglycans influences the interaction with LDL, for which the degree of sulfation affects the interaction of LDL with proteoglycans. Sambandam T. y col. Arterioascler Thromb, 11: 561-568 (1991)

Moreover, oxidized LDL can be internalized by macrophages via scavenger receptors on the surface of these cells, leading to intracellular cholesterol accumulation with subsequent foam cell formation. These events represent the main steps to initiate the inflammatory response, with the involvement of monocytes/macrophages, mast cells, dendritic cells, T cells and NKT. Camejo, G. y col. Atherosclerosis 139(2): 205-22 (1998); Hurt-Camejo, E. y col. Invest Clin 42 Suppl 1:43-73 (2001); Skalen, K., M. y col. Nature 417:750-754 (2002). There are experimental evidences demonstrating the involvement of proteoglycans present on the surface of macrophages in the binding of oxidized LDL to these cells and in the internalization or incorporation of these particles, which finally causes foam cell formation. Halvorsen B. y col. Biochem J. 331:743-752 (1998).

It is indisputable that the adoptions of healthier lifestyles in conjunction with the use of anti-thrombotic and lipid-reducing agents have had an impact on reducing the risk of developing cardiovascular events, but these strategies are still insufficient to fully eliminate these risks.

As mentioned above, atherosclerosis is a multifactorial inflammatory disease where multiple antigens are important in their development, so different strategies are being developed for active and passive immunotherapy with the aim of achieving greater therapeutic impact on this disease.

One of these strategies is therapies to increase HDL, due to the inverse relationship between HDL-cholesterol and cardiovascular disease. The CETP is a key enzyme in the metabolism of HDL and is considered a potential target for therapy because the reduction of its activity increases HDL levels. The strategy of using vaccines inducing Abs able to bind and inhibit the function of CETP has been described in WO 1997/041227 y WO 2006/133196. However, recent studies showing the failure of a Phase III clinical trial using the CETP inhibitor Torcetrapib have cast doubt on this strategy. Nicholls S. J. y col. Circulation. 9; 118:2506-14 (2008); Hermann M. y col. Curr Hypertens Rep, 11:76-80 (2009). Some authors have described vaccines using oxidized LDL as immunogens in order to inhibit the formation of atherosclerotic plaques. Palinski W. y col. Proc. Natl. Acad. Sci. USA 92:821-25 (1995); Ameli S y col. Arterioscler. Thromb. Vasc. Biol. 16:1074-79 (1996); Freigang S. y col. Arterioscl. Thromb. Vasc. Biol. 18:1972-82 9 (1998); Zhou X. y col. Arterioscler. Thromb. Vasc. Biol. 21:108-14 (2001); George J. y col. Atherosclerosis 138:147-52 (1998); Fredrikson G. N. y col. Arterioscler. Thromb. Vasc. Biol. 23:879-84 (2003); US 2008/0070265A1.

Another strategy is the development of prophylactic and therapeutic vaccines based on specific fragments of apolipoprotein C-III oxidized, with the aim of inducing an immune response capable of preventing or reducing formation of atherosclerotic lesions (WO 2001/064008, WO 2003/020765, WO 2004/080375 y WO 2004/081045).

Another vaccine approach described is based on a peptide conjugated to an aldehyde such as MDA or 4-HNE to induce Abs that interact with alpha/beta receptors of T cells, preventing the formation of atherosclerotic lesions (WO2001/068119).

Some authors have advocated for the importance of vaccines against pathogens in atherosclerosis to prevent the development of atherosclerotic plaques (WO1998/033510, US 006291437 B1, U.S. Pat. No. 6,471,965 B1, US006808713 B1).

Another proposed strategy to delay or reduce the severity of atherosclerosis, caused by ingestion of dietary cholesterol, is the use of vaccines against sterols (US 2002/0018808 A1).

Passive immunotherapy as a therapeutic tool can also play an important role in atherosclerosis. Passive immunization to treat or prevent atherosclerosis by using human Abs against oxidized or modified fragments of Apo B100 has been described (US 005196324[a], US 2007/0098725 A1, US 2008/0075716 A1).

Additionally, passive immunization with specific Abs for phosphorylcholine has been proposed as a therapeutic combination for the treatment or prevention of atherosclerosis (US 2007/0286868 A1, US 2007/0122419 A1).

Another strategy described is the use of Abs or antigen binding fragments that specifically bind to human M-CSF (US 2007326414 B2).

The use of MAb that prevent adhesion of monocytes to vascular endothelium and thus prevent the invasion to endothelium and surrounding tissues by these cells, is another therapeutic approach for this disease (US 005541296 A).

It has been described the use of monoclonal Abs as inhibitors of the glycoprotein IIb/IIIa receptor and thus of platelet aggregation (WO 1999/052551, US 005976532 A).

In addition, human monoclonal Abs were obtained against the protective peptide epitopes of the CIII apolipoprotein for using in passive immunotherapy (WO 2004/081046).

Also, the use of intravenous immunoglobulin (IVIG) may have an atheroprotective effect. Udi N y y col. Autoimmunity reviews 7:445-452 (2008). Chimeric MAbs that react with sulfatides and sulfated glycosaminoglycans, or that recognize macrophages and atherosclerotic lesions, with the ability of inhibiting the formation of atherosclerotic lesions when administered at low doses and inducing an antibody response against these sulfated molecules have not been described.

DETAILED DESCRIPTION OF THE INVENTION

The present invention relates to monoclonal Abs characterized for the recognition of sulfated and sulfated proteoglycans or fragments derived from them.

The anti-sulfatide and anti-sulfated proteoglycans Abs of the invention are preferably monoclonals. Within the scope of the invention are also included Ab fragments such as Fab fragments, Fab', Fab'-SH and F (ab')2 of the anti-sulfatide and anti-sulfated proteoglycan Abs provided in the present specification. These Ab fragments can be created by traditional means, such as enzymatic digestion, or can be produced by recombinant techniques. These Ab fragments may be chimeric or humanized. These fragments are useful for diagnostic and therapeutic purposes set forth in this description. The invention also includes embodiments of substantially pure Abs and fragments.

In a particular embodiment, the Ab of the present invention is characterized by the following sequences of the variable region of heavy and light chains:

| Heavy chain: | | |
|---|---|---|
| HCDR1 | SEQ ID: 1 | RYSVH |
| HCDR2 | SEQ ID: 2 | MIWGGGSTDYNSALKS |
| HCDR3 | SEQ ID: 3 | SGVRRGRAQAWFAY |
| HFR1 | SEQ ID: 7 | QVQLKESGPGLVAPSQSLSITCTVSGFSLS |
| HFR2 | SEQ ID: 8 | WVRQPPGKGLEWLG |
| HFR3 | SEQ ID: 9 | RLSISKDNSKSQVFLKMNSLQTDDTAMYYCAR |
| HFR4 | SEQ ID: 10 | WGQGTLVTVSA |

| Light chain: | | |
|---|---|---|
| LCDR1 | SEQ ID: 4 | KASQDVSTAVA |
| LCDR2 | SEQ ID: 5 | SASYRYT |
| LCDR3 | SEQ ID: 6 | QQHYSTPWT |
| LFR1 | SEQ ID: 11 | DIVMTQSHKFMSTSVGDRVSITC |
| LFR2 | SEQ ID: 12 | WYQQKPGQSPKLLIY |
| LFR3 | SEQ ID: 13 | GVPDRFTGSGSGTDFTFTISSVQAEDLAVYYC |
| LFR4 | SEQ ID: 14 | FGGGTKLELK |

Additionally, the antibody of the invention includes human IgG1 constant regions for heavy chain and human Cκ for light chain.

This invention encompasses compositions, including pharmaceutical compositions, which comprise an antibody anti-sulfatides and anti-sulfated proteoglycans of the invention or fragments derived therefrom. As used in this specification, the compositions comprise one or more Abs that bind to sulfatides and sulfated proteoglycans.

These compositions may further comprise suitable carriers, such as pharmaceutically acceptable excipients including buffered solutions or adjuvants, which are well known in the state of the art.

In another embodiment the present invention relates to the pharmaceutical composition comprising the MAb whose variable region sequences of heavy and light chains are shown below.

| Heavy chain: | | |
|---|---|---|
| HCDR1 | SEQ ID: 1 | RYSVH |
| HCDR2 | SEQ ID: 2 | MIWGGGSTDYNSALKS |

-continued

```
HCDR3 SEQ ID: 3  SGVRRGRAQAWFAY
HFR1  SEQ ID: 7  QVQLKESGPGLVAPSQSLSITCTVSGFSLS
HFR2  SEQ ID: 8  WVRQPPGKGLEWLG
HFR3  SEQ ID: 9  RLSISKDNSKSQVFLKMNSLQTDDTAMYYCAR
HFR4  SEQ ID: 10 WGQGTLVTVSA
                 Light chain:
LCDR1 SEQ ID: 4  KASQDVSTAVA
LCDR2 SEQ ID: 5  SASYRYT
LCDR3 SEQ ID: 6  QQHYSTPWT
LFR1  SEQ ID: 11 DIVMTQSHKFMSTSVGDRVSITC
LFR2  SEQ ID: 12 WYQQKPGQSPKLLIY
LFR3  SEQ ID: 13 GVPDRFTGSGSGTDFTFTISSVQAEDLAVYYC
LFR4  SEQ ID: 14 FGGGTKLELK
```

In a third aspect, the present invention relates to a kit of reagents useful in diagnosis of atherosclerotic lesions, including one of the Abs of the invention or fragments derived therefrom. And more particularly the set of reagents comprising the MAb with the sequences of the variable region of heavy and light chains described above.

In a further aspect the present invention relates to the use of Abs of the invention for the treatment of cardiovascular diseases, particularly those that show evidence of atherosclerotic lesions.

The term antibody generally refers to a MAb and more particularly to a murine MAb or chimeric Ab.

Obtaining the Antibody:

In general, the anti-sulfatide and anti-sulfated proteoglycans-MAbs of the invention can be obtained by the hybridoma method, first described in Kohler et al., Nature, 256:495 (1975), from mice immunized with glycolipidic extracts obtained from natural or synthetic sources. The spleen cells from immunized mice are fused with myeloma cells P3.X63Ag8 6.5.3, cultured in selective medium as described and producing clones are selected by detection of immunoglobulins in the culture supernatant by ELISA.

After identifying the hybridoma cells that produce Abs with the desired specificity, affinity and/or activity, the Ab producing clones can be subcloned by limiting dilution procedures and can be grown by standard methods of cell culture growth (Goding, Monoclonal Abs: Principles and Practice, págs. 59-103 (Academic Press, 1986)). Culture media suitable for this purpose include, for example, medium D-MEM or RPMI-1640. Furthermore, hybridoma cells can be grown in vivo in an animal in the form of ascites tumor.

MAbs secreted by the subclones are suitably separated from the culture medium, ascites fluid or serum by conventional procedures for purification of immunoglobulins, for example, protein A-sepharose, hydroxylapatite chromatography, gel electrophoresis, dialysis or affinity chromatography.

The Abs of the invention can also be obtained by genetic engineering techniques properly manipulating murine immunoglobulin genes. For example, chimeric Abs of the invention can be obtained from RNA purified from cells producing murine monoclonal Abs by conventional techniques for manipulation of genes, such as amplification, cloning, gene sequencing and digestion, among other described in the state of the art, for example in Sambrook et al., Molecular Cloning: A Laboratory Manual 3rd. edition (2001) Cold Spring Harbor Laboratory Press, Cold Spring Harbor, N.Y. Current Protocols in molecular biology (F. M. Ausubel, et al. eds., (2003)); la serie Methods in Enzimology (Academic Press, Inc.): PCR 2: A practical approach (M. J. MacPherson, B. D. Hames y G. R. Taylor eds. (1995)), Harlow y Lane, eds. (1988) ABS, A laboratory manual, y Animal cell culture (R. I. Freshney, ed. (1987)).

cDNA synthesis and PCR amplification (the acronym of Polymerase Chain Reaction) of Ab variable regions can be performed from RNA that encodes the murine Ab, cDNA is synthesized, VK and VH variable regions are amplified by PCR, this can be done by following the conventional techniques described for the purpose in the state of the art.

The products of PCRs for each of the heavy and light chains, respectively, were cloned into the vectors used for gene sequencing. The resulting clones are sequenced using any of the methods described for this purpose, for example, the dideoxynucleotides method using T7 DNA Polymerase according to manufacturer's specifications.

The variable region genes of heavy VH and light VK chains are obtained by enzymatic restriction of the intermediate constructions and are cloned into the respective expression vectors according to conventional techniques for construction of chimeric genes. For such purposes are useful any of the described vectors for efficient expression of recombinant proteins particularly MAbs.

For the expression of the chimeric Ab NS0 cells can be used, which are electroporated with DNA constructs in the respective expression vectors containing the Ab genes. These cells grow in the selective medium. The detection of immunoglobulin-producing clones is performed by the measurement in the supernatant of the cultures using an ELISA (enzyme linked immunosorbent assay).

Selection of Abs with the Desired Specificity and Function:

In certain embodiments, Abs of the present invention can be detected by various techniques described for this purpose in the state of the art, for example, by an ELISA.

In certain embodiments of the invention the biological activity of the Abs produced is analyzed. In some embodiments, the Abs of the invention are tested for their antigen binding activity.

The antigen binding assays known in the specialty and that can be used in the present specification include, among others, direct or competitive binding assays that use techniques such as Western blot, radioimmunoassays, ELISA, double antibody immunoassay (sandwich), immunoprecipitation assays, fluorescent immunoassays and protein A immunoassays. The illustrative assays for antigen binding are included later in the Examples section.

Additionally, In the present invention those clones that produce Abs capable of recognizing atherosclerotic plaques in human aorta tissue sections can be identified, this can be done using conventional immunohistochemical techniques described in the state of the art.

In another aspect the ability to induce anti-heparin response in mice by Abs of the present invention can be measured. For this, different groups of animals are immunized with the Abs of the invention and serum samples of these animals are tested for the presence of anti-heparin Abs.

In an additional aspect the anti-atherosclerotic effect of the Abs of the present invention can be measured, and for this a model of induction of atherosclerotic lesions in rabbits with Lipofundin can be used. (Takacs E, Harsing J, Fuzesi S, Jellinek H.1986 Arteriosclerosis developing in rabbits after lipofundin administration. Morphol Igazsagugyi Ory Sz. 26:99-105; Noa M & Mas R (1992).

Pharmaceutical Composition:

In one embodiment, the invention provides a pharmaceutical composition that comprises one or more Abs of the present invention. In one embodiment, a composition comprising an antibody further comprises an excipient which is pharmaceutically acceptable In one aspect, the invention provides a kit of reagents comprising one or more Abs of the invention, and additionally can comprise a buffer solution. In one embodiment, the solution buffer is pharmaceutically acceptable. In one embodiment, a composition comprising an Ab also includes a carrier molecule, which in some embodiments is pharmaceutically acceptable. In one embodiment, a reagent kit also includes instructions for the administration or use of the composition (eg, Ab to a subject.

The pharmaceutical compositions comprising an Ab of the invention are prepared for their conservation by mixing the Abs with the desired degree of purity with carrier molecules, optional excipients or stabilizers physiologically acceptable (Remington: The Science and Practice of Pharmacy 20th edition (2000)), in the form of aqueous solutions, lyophilized or other lyophilized formulations. The acceptable vehicles, excipients, or stabilizers are non-toxic to recipients at all doses and concentrations employed.

The MAbs of the invention are present in the pharmaceutical composition in combination in amounts that are effective for the intended purpose.

Formulations for in vivo administration must be sterile. This is achieved by filtration through sterile filtration membranes.

In one aspect, the invention shows how to use an Ab of the invention in the preparation of a drug for therapeutic and/or prophylactic treatment of a disorder, such as cardiovascular disease.

The Abs of the invention can be used to treat, inhibit, delay progression, prevent/delay onset of atherosclerotic lesions, improve or prevent diseases, disorders or processes associated with the expression and/or activity of one or more antigenic molecules.

According to the present invention, a therapeutic dose of these Abs would be in the ranging between 10 micrograms and 10 mg per dose, preferably between 100 microgram and 1 mg per dose.

The MAb(s) of the invention is(are) administered by any appropriate means, including parenteral, subcutaneous, intraperitoneal, intrapulmonary and intranasal routes, and, if desired for local treatment, intralesional route.

In another aspect, the invention provides a kit of reagents for diagnosing a disorder, such as cardiovascular disease.

EXAMPLES

The following examples are intended to illustrate the invention without limiting its scope.

In the following examples all restriction or modification enzymes as well as reagents and materials used were obtained from commercial sources unless otherwise specified.

Example 1

Recognition by the Chimeric MAb Anti-SO3 of Bovine Brain Sulfatides

Using ELISA, PolySorp plates, Nunc, were coated with 50 µL/well of a solution of bovine brain sulfatides at a concentration of 4 µg/mL in methanol and the solvent was evaporated by incubating for 90 minutes at 37° C. Then plates were blocked with 200 µL/well of phosphate buffered saline (PBS) containing 1% bovine serum albumin (SAB) for one hour at room temperature. Later, 50 µL/well were added of different concentrations of chimeric antibody anti-SO3 in PBS and incubated for one hour at 37° C. Then plates were washed with PBS and 50 µL/well of a goat antiserum anti-human gamma chain conjugated to alkaline phosphatase (Sigma) were added. After incubating the plates for 1 hour at 37° C., they were washed again and 100 µL/well of substrate solution consisting of 1 mg/mL p-nitrophenylphosphate in diethanolamine buffer, pH 9, 8, were added. The absorbance of the reaction product was measured in an ELISA reader at 405 nm after 30 minutes incubation at room temperature.

As a negative control a chimeric MAb modified by the replacement of R by S in the variable region of heavy chain at position 98 of the chimeric monoclonal anti-SO3- was used. FIG. 1 shows reactivity against sulfatides of the different chimeric MAbs. The graph shows that the chimeric monoclonal anti-SO3-recognizes sulfatides even at a concentration as low as 0.01 mg/ml. In contrast, the chimeric MAb modified at position 98 did not show any reactivity.

Example 2

Heparin Recognition Test

Subsequently it was assessed whether the chimeric monoclonal anti-SO3-recognized sulfated molecules more complex than sulfatides. For the study it was chosen heparin, a highly sulfated molecule that is used as a model of sulfated glycosaminoglycans.

The assay for anti-heparin reactivity was made based on the ELISA technique for biglican developed by Skalen, K. M. y cols (Nature 417: 750-754, 2002), with slight modifications. Maxisorp microtiter plates (Nunc) were coated with heparin (Sigma) at 10 µg/mL (100 µL/well) in Hepes buffered saline solution (HBSS) (20 mM Hepes, 150 mM NaCl, pH 7.4) and incubated overnight at 4° C. Plates were washed three times with HBSS and then blocked with HBSS containing 1% SAB (HBSS-BSA) for one hour at room temperature. Plates were washed three times with HBSS-Tween 20 0.02% (HBSS-T) and serial dilutions of chimeric monoclonal anti-SO3- were added, from an initial concentration of 40 µg/mL in binding buffer (10 mM Hepes, 20 mM NaCl, 2 mM $CaCl_2$, 2 mM $MgCl_2$, pH 7.4), during one hour at room temperature. As a negative control the chimeric Ab modified by the replacement of R by S in the variable region of heavy chain at position 98 of the chimeric monoclonal anti-SO3- was used. Plates were washed twice with HBSS-T and then incubated for one hour at room temperature with a goat antiserum anti-human gamma chain conjugated to alkaline phosphatase (Sigma-Aldrich, USA) in HBSS-T containing 0.1 SAB %. Required washes were performed and the reaction was developed using the substrate p-nitrophenylphosphate dissolved in diethanolamine buffer, pH 9.8. The absorbance at 405 nm of the product was quantified in an ELISA reader (Organon Teknica, Austria).

As shown in FIG. 2, the chimeric monoclonal anti-SO3- had a high reactivity against heparin. In contrast, the modified chimeric Ab used as isotype control showed no reactivity at any of the studied concentrations.

Example 3

Recognition of the J774 Cell Line by Flow Cytometry

The monocytes and macrophages are important in inflammatory processes, such as atherosclerosis (Østerud B Björklid E. Physiol Rev 83:1069-1112, 2003). These cells synthesize proteoglycans and it has been shown that some of the ways to incorporate oxidized LDL by macrophages in the formation of foam cells involve the cell membrane proteoglycans (Halvorsen B, et al. Biochem J. 331:743-752, 1998).

To determine whether anti-SO3-chimeric Ab was able to recognize macrophages, we carried out flow cytometry experiments using the murine macrophage cell line J774, which was cultured in DMEM-F12 (Gibco BRL, Paisley, Scotland) supplemented with 8% inactivated serum fetal calf (SFT; Gibco), 2 mM L-glutamine, 100 U/mL penicillin, 100 µg/mL streptomycin.

The cells ($0.5 \times 10^6$ per tube) were incubated with 20 µL/tube of inactivated rabbit serum for 10 minutes at 37° C. to block Fc-gamma receptors. Subsequently, anti-SO3-chimeric MAb and the isotype-control modified chimeric Ab were added, both biotinylated, at 10 µg/mL in PBS, pH 7.4, containing 1% bovine serum albumin (Sigma, St. Louis, Mo.) and 0.01% sodium azide for 30 minutes in an ice bath. After washing the cells, they were incubated with a streptavidin-fluorescein isothiocyanate complex (Jackson Immunoresearch Laboratories, West Grove, Pa.) at 1/200 dilution, for 30 minutes in an ice bath. The cells were washed, resuspended in PBS containing 1% sodium azide and analyzed on a flow cytometer (Becton-Dickinson, San Jose, Calif.).

As shown in FIG. 3, the chimeric Ab used as isotype control, did not recognize the cell line J774. In contrast, the anti-SO3-chimeric Ab recognized 93.7% of the cells.

Example 4

Recognition of Atherosclerotic Plaque in Human Aorta

The immunohistochemistry determination of chimeric Ab anti-SO3-recognition was performed on fragments of human aorta fixed in formalin and embedded in paraffin. Tissue sections of 4 µm were used, which were mounted on silanized slides and incubated at 68° C. for 12 hours. The tissue sections were deparaffined in xylol and hydrated in ethanol at decreasing concentrations. Then they were washed for 5 minutes in distilled water and washed in PBS. Antigen unmasking was performed using a thermostatic bath set at a temperature of 100° C. The plates immersed in citrate buffer pH 6.0 remained in the bath for 30 minutes and then were boiled in citrate buffer pH 6.8 for 10 minutes using a microwave oven. The slices were left to cool for 20 minutes and then were washed with distilled water and PBS. The endogenous peroxidase was inhibited with a solution of $H_2O_2$ 3% for 10 minutes at room temperature, washed with PBS, and biotinylated chimeric Ab anti-SO3- and isotype control Ab were added at a concentration of 50 µg/mL for 30 minutes at room temperature. Later, slides were washed with PBS and a streptavidin-peroxidase complex (Anacrom Diagnostics) was added for the same time and temperature. Finally, tissue sections were incubated with a fresh mixture solution of 3,3'-diaminobenzidine (DAB) in 1 mL of substrate buffer for 3 to 5 min. The contrast was performed with Mayer's hematoxylin, samples were dehydrated in increasing alcohol concentrations, clarified in xylol and finally mounted in permanent medium plates Eukitt (Kinder GmbH & Co.). The evaluation was performed using a white light microscope (Leica).

FIG. 4 shows how the anti-SO3-chimeric Ab reacted intensely with samples of atherosclerotic lesions present in the aorta. It was observed reactivity with lipid-laden macrophages or foam cells and with lesion lipid core (reactivity is shown in deep brown color). The figure shows how the Ab used as isotype control did not recognize the human aorta sections.

Example 5

Ability to Induce Anti-Heparin Response in Mice by the Anti-SO3 Chimeric Ab

Ten BALB/c female mice were used; they received subcutaneously 50 µg of anti-SO3-chimeric Ab in 200 µL. Immunizations were performed every 14 days to complete a total of four doses. The anti-SO3-chimeric Ab was administered without adjuvant or carrier protein. Serum samples were taken on days 0 and 49 (seven days after the fourth dose).

The presence of anti-heparin Abs in the serum of immunized animals was measured using the ELISA technique described in Example 2, using Maxisorp plates coated with heparin (10 µg/mL, 100 µL/well). The sera of mice were tested at 1/100 dilution in binding buffer, 100 µL/well. As secondary antibody a goat anti-mouse IgG and IgM antiserum conjugated to alkaline phosphatase (Jackson) was used.

FIG. 5 shows the results of the assay with the sera of mice taken on days 0 and 49. It was not detected the presence of anti-heparin Abs in the preimmune sera (day 0) of any animal. In contrast, the presence of these serum Abs after mice were immunized with the anti-SO3-chimeric Ab was detected. This result indicates that the anti-SO3-chimeric Ab not only recognizes strongly the heparin, but has the surprising ability to induce a response against this molecule (vaccine effect).

Example 6

Anti-Atherosclerotic Effect of Anti-SO3-Chimeric Ab

To assess whether the anti-SO3-chimeric Ab was capable to produce a biological effect in vivo, we used a model previously described, of induction of atherosclerotic lesions in rabbits with Lipofundin (Takács E and cols. Morphol Igazságügyi Ory Sz. 26:99-105, 1998, Noa M & R. More Progress in Medical Sciences, 6: 14-19, 1992).

Fifteen New Zealand rabbits divided into three groups of five rabbits were used. Group 1 received no treatment (negative control). Group 2 received daily, for eight days, 2 mL per kg of Lipofundin 20% (Braun), intravenously. To group 3 was given three doses of 100 pg of anti-SO3-chimeric Ab in PBS, subcutaneously, at intervals of seven days, and the day of the last immunization started the daily administration of Lipofundin with the same scheme that was used in animals of group 2. All rabbits were sacrificed under anesthesia one day after receiving the last dose of Lipofundin and negative control animals of group 1 were sacrificed the same day. Aortas were obtained from animals and the pathological study to determine the presence of macroscopic and microscopic atherosclerotic lesions was performed.

The aortas of rabbits from group 1, who received no treatment, showed no gross lesions. In all aortas from rabbits in group 2, which received 2 mL of Lipofundin per kg for eight days, gross lesions were observed. In the aortas of rabbits that previously received three doses of the anti-SO3-chimeric Ab and then were administered with Lipofundin, there were no macroscopic lesions.

For the study of microscopic lesions, fragments of the aortas were fixed in formalin and embedded in paraffin. Tissue sections of 4 µm were used, mounted on silanized slides and stained with hematoxylin-eosin. The evaluation was performed using a white light microscope (Leica).

When the tissue sections of aorta of rabbits that received no treatment were evaluated, all showed the normal structure of the arteries without no alterations, as shown in FIG. 6. In aorta sections from all rabbits of the group that received Lipofundin characteristic lesions were observed: presence of intima thickening, with deposits of extracellular material between muscle, elastic and collagen fibers, and tissue architecture distortion. In contrast, samples from three rabbits that received three doses of anti-SO3-chimeric Ab and then were administered with Lipofundin, no microscopic lesions were observed. In the samples from the remaining two rabbits tissue alterations consisting in some discrete thickening in some areas of the arterial wall, with a deposit of extracellular material between the fibers, were observed. There was no intimal thickening.

Various concentrations of the anti-SO3-chimeric MAb and isotype control chimeric MAbs were added to ELISA plates coated with sulfatides at a concentration of 4 µg/mL in methanol. The reactivity was detected with goat anti-human gamma chain antiserum conjugated to alkaline phosphatase. The absorbance at 405 nm of the product was quantified in an ELISA reader. (*$p<0.05$, Mann-Whitney U test).

Figure 1:
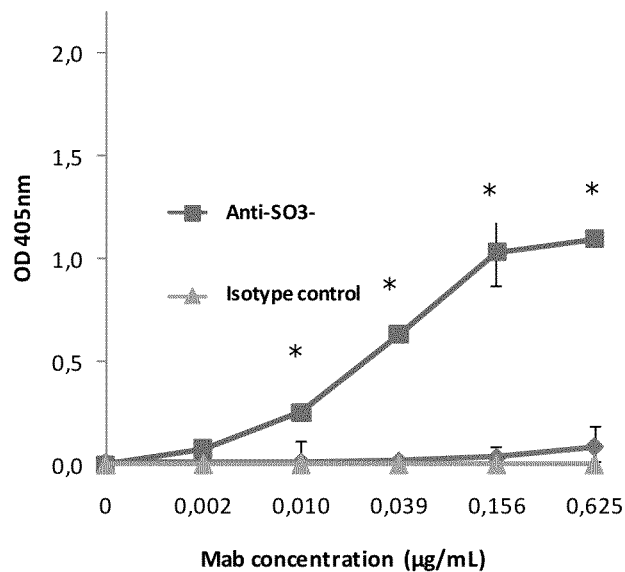
FIG. 1. Recognition of sulphatides by anti-SO3-chimeric MAb.
Figure 2:
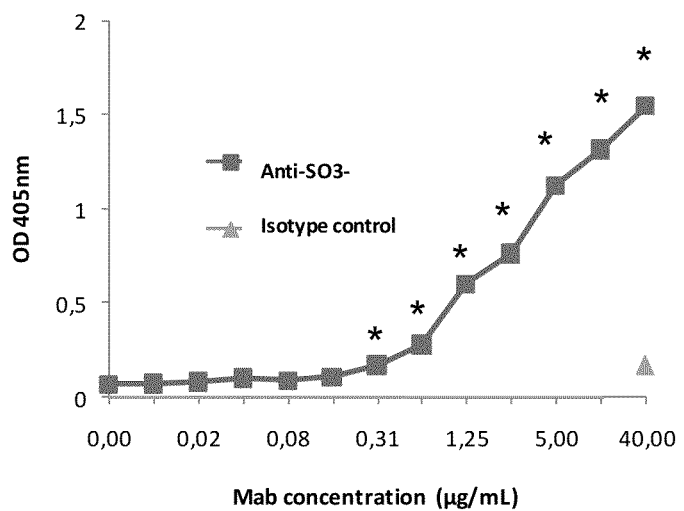

FIG. 2. Heparin recognition by anti-SO3-chimeric MAb.

Various concentrations of the anti-SO3-chimeric MAb and the isotype control chimeric MAb were added to ELISA plates coated with heparin at concentration of 10 µg/mL in HBSS. The reactivity was detected with a goat anti-human gamma chain antiserum conjugated to alkaline phosphatase. The absorbance at 405 nm of the product was quantified in an ELISA reader. (*$p<0.05$, Mann-Whitney U test).

Figure 3:
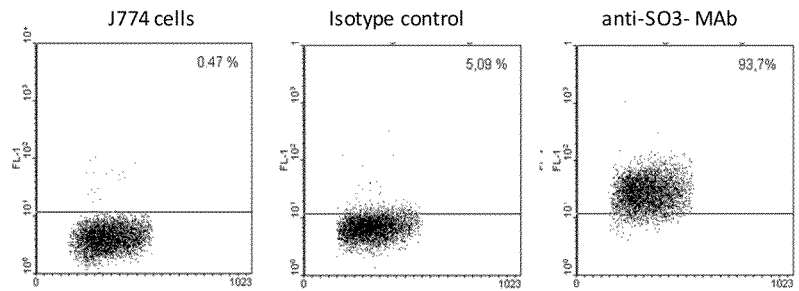

FIG. 3. Recognition of the J774 cell line by the anti-SO3-chimeric MAb.

The cells were incubated with 10 µg/mL of the biotinylated Abs. The reaction was revealed with a goat anti-human IgG antiserum conjugated to FITC and analyzed by flow cytometry.

Figure 4:
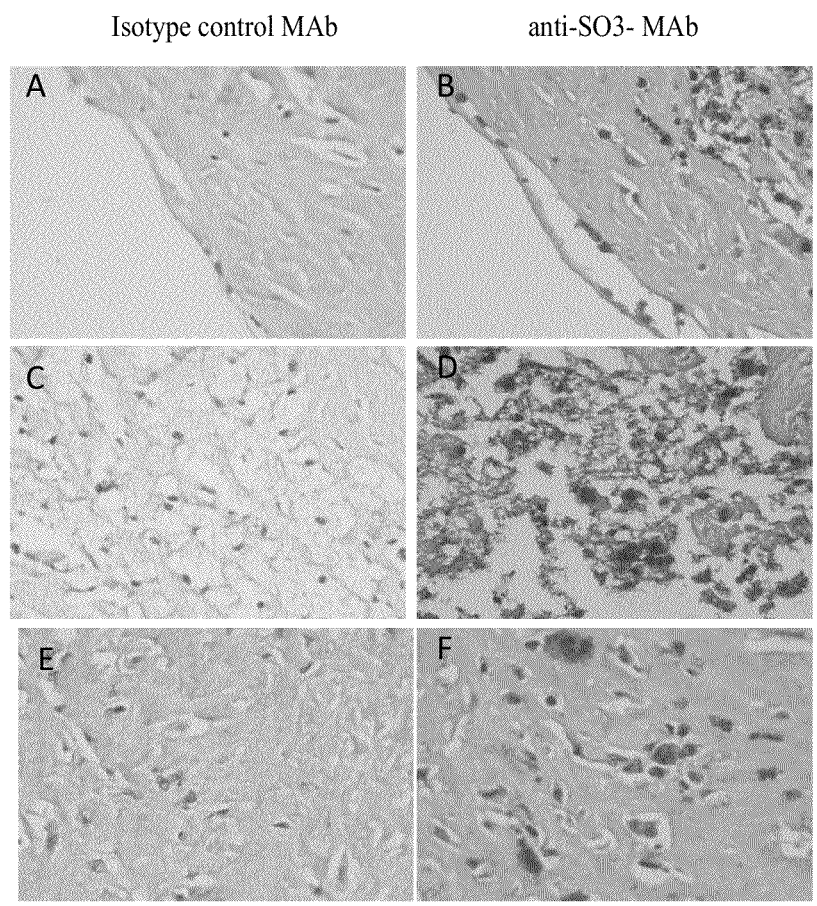

FIG. 4. Human atherosclerotic plaques recognition by the anti-SO3-chimeric MAb.

Fragments of human aorta fixed in formalin and embedded in paraffin (4 µm) were incubated with biotinylated anti-SO3-chimeric Ab and isotype control Ab. The reaction was revealed with a streptavidin-peroxidase complex. The epitopes recognized by anti-SO3-MAb are indicated by the intense brown color and the nuclei of the cells were counterstained with hematoxylin. (400×).

Figure 5:
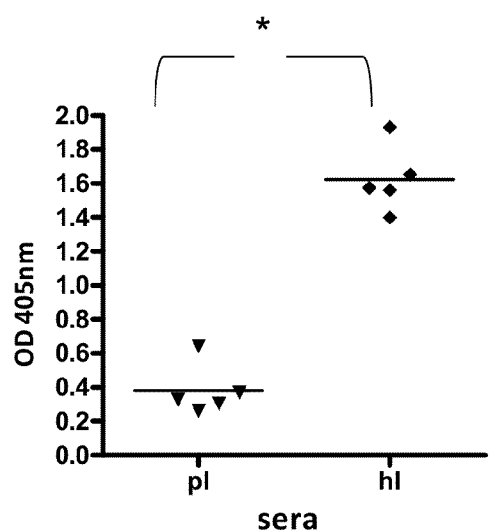

FIG. 5: Abs response against heparin induced by immunization with the anti-SO3-chimeric MAb.

Serum samples obtained from BALB/c mice on days 0 and 49 of the immunization scheme with the anti-SO3-chimeric MAb were assayed by ELISA. Each symbol is the value obtained with the serum of a mouse. pI and hI: preimmune and hyperimmune, respectively (*$p<0.05$, Mann-Whitney U test).

Figure 6:
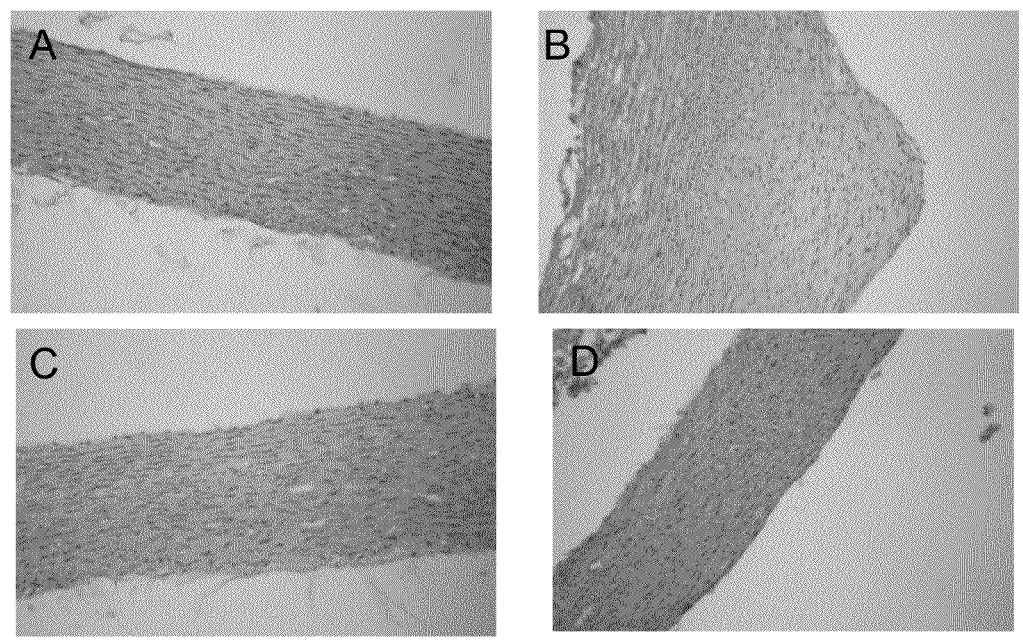

FIG. 6: Effect of treatment with anti-SO3-chimeric MAb in the development of atherosclerotic lesions in Lipofundin model in rabbits.

Histological sections of rabbit thoracic aortas representative of different groups of studies. (A) Group 1, untreated animal, which shows the normal structure of the arteries, without alterations. (B) Group 2, animals treated with Lipofundin, where arterial intima thickening is observed, with deposits of extracellular material between the muscle, elastic and collagen fibers, and distortion of tissue architecture. (C and D) Group 3, animals immunized with the anti-SO3-chimeric MAb and which later received Lipofundin; no obvious tissue damage or intima thickening were observed. Hematoxylin-eosin stain 180×

The invention claimed is:

1. A monoclonal antibody which specifically binds sulfatides and sulfated proteoglycans, said monoclonal antibody having complementarity determining regions (CDRs) of variable regions of heavy and light chains as follows:

```
                    Heavy chain

HCDR1 SEQ ID: 1 RYSVH

HCDR2 SEQ ID: 2 MIWGGGSTDYNSALKS

HCDR3 SEQ ID: 3 SGVRRGRAQAWFAY
                    Light chain:

LCDR1 SEQ ID: 4 KASQDVSTAVA

LCDR2 SEQ ID: 5 SASYRYT

LCDR3 SEQ ID: 6 QQHYSTPWT.
```

2. The monoclonal antibody according to claim 1, wherein the sequences of framework regions within the variable region of heavy and light chains are shown below:

```
                    Heavy chain

HFR1 SEQ ID: 7 QVQLKESGPGLVAPSQSLSITCTVSGFSLS

HFR2 SEQ ID: 8 WVRQPPGKGLEWLG

HFR3 SEQ ID: 9 RLSISKDNSKSQVFLKMNSLQTDDTAMYYCAR

HFR4 SEQ ID: 10 WGQGTLVTVSA
                    Light chain:

LFR1 SEQ ID: 11 DIVMTQSHKFMSTSVGDRVSITC

LFR2 SEQ ID: 12 WYQQKPGQSPKLLIY

LFR3 SEQ ID: 13 GVPDRFTGSGSGTDFTFTISSVQAEDLAVYYC

LFR4 SEQ ID: 14 FGGGTKLELK.
```

3. The monoclonal antibody according to claim 2 wherein the sequences of the constant regions are human IgG1 for heavy chain and Ck for the light chain.

4. A pharmaceutical composition comprising any of the monoclonal antibodies of claim 1 or fragments thereof.

5. The pharmaceutical composition of claim 4 further comprising a pharmaceutically acceptable excipient.

6. The pharmaceutical composition of claim 5 further comprising an adjuvant.

7. A kit of reagents useful in diagnosis of atherosclerotic lesions comprising any of the monoclonal antibodies of claim 1 or fragments thereof.

8. A method of treating atherosclerosis comprising administering to a patient in need thereof an effective amount of the monoclonal antibody of claim 1.

9. A method of diagnosing atherosclerosis in a patient comprising obtaining a serum sample from said patient, conducting a direct or competitive binding assay using the monoclonal antibody of claim 1 to recognize sulfatides and/or sulfated proteoglycans in said sample, wherein recognition of sulfatides and/or sulfated proteoglycans is indicative of atherosclerosis.

\* \* \* \* \*